(12) United States Patent
Reddy et al.

(10) Patent No.: US 12,717,357 B2
(45) Date of Patent: Aug. 25, 2026

(54) WATER LEVEL MANAGEMENT SYSTEM

(71) Applicant: Swim Sense, LLC, Boca Raton, FL (US)

(72) Inventors: Rakesh Reddy, Boca Raton, FL (US); Kevin Doyle, Boca Raton, FL (US)

(73) Assignee: Swim Sense, LLC, Boca Raton, FL (US)

( * ) Notice: Subject to any disclaimer, the term of this patent is extended or adjusted under 35 U.S.C. 154(b) by 27 days.

(21) Appl. No.: 18/413,157

(22) Filed: Jan. 16, 2024

(65) Prior Publication Data

US 2024/0255973 A1 Aug. 1, 2024

Related U.S. Application Data

(60) Provisional application No. 63/441,509, filed on Jan. 27, 2023.

(51) Int. Cl.

| | |
|---|---|
| ***G05D 9/12*** | (2006.01) |
| ***A61L 2/10*** | (2006.01) |
| ***A61L 2/24*** | (2006.01) |
| ***A61L 2/26*** | (2006.01) |

(52) U.S. Cl.

CPC .................. *G05D 9/12* (2013.01); *A61L 2/10* (2013.01); *A61L 2/24* (2013.01); *A61L 2/26* (2013.01); *A61L 2202/11* (2013.01); *A61L 2202/14* (2013.01)

(58) Field of Classification Search

CPC ....... G05D 9/12; E04H 4/12; Y10T 137/7306; G01F 23/296

See application file for complete search history.

(56) References Cited

U.S. PATENT DOCUMENTS 2,739,939 A * 3/1956 Leslie ...................... G05D 9/02 210/114
3,759,286 A * 9/1973 Page ........................ G05D 9/12 137/392

(Continued)

FOREIGN PATENT DOCUMENTS

CN 217498745 U * 9/2022

OTHER PUBLICATIONS

English Machine Translation of CN_217498745U (Year: 2022).*

*Primary Examiner* — Reinaldo Sanchez-Medina
*Assistant Examiner* — Nicole Gardner
(74) *Attorney, Agent, or Firm* — Armon Shahdadi; Pierson Ferdinand LLP

(57) ABSTRACT

Examples described herein include systems and methods for improved water level management in a body of water, such as a pool, spa, or pond. An example system includes a water sensor in a static pipe connected to a body of water, a processor receiving signals from the sensor, a memory, and a battery charged via a low-power data channel. When the sensor detects a low-water-level condition, the system opens a fill valve to add water to the body of water. An ultraviolet light can illuminate a portion of the pipe for purposes of preventing algae growth, and an orientation sensor provides a level of safety by deactivating the light for orientations outside a threshold range that could indicate installation or maintenance on the system. The system components can all be contained in a housing that can be mounted to an end of the static pipe.

17 Claims, 4 Drawing Sheets

(56) References Cited

U.S. PATENT DOCUMENTS

| | | | | | |
|---|---|---|---|---|---|
| 3,809,116 | A * | 5/1974 | Sanner | G01F 23/241 | 137/391 |
| 4,342,125 | A * | 8/1982 | Hodge | E04H 4/12 | 137/430 |
| 4,380,091 | A * | 4/1983 | Lively | E04H 4/12 | 137/391 |
| 5,365,617 | A * | 11/1994 | Tarr | E04H 4/12 | 137/392 |
| 6,006,605 | A * | 12/1999 | Sulollari | E04H 4/12 | 73/306 |
| 6,223,359 | B1 * | 5/2001 | Oltmanns | E04H 4/12 | 137/392 |
| 6,276,200 | B1 * | 8/2001 | Cazden | G01F 23/62 | 73/309 |
| 2015/0227145 | A1 * | 8/2015 | Reddy | G05D 9/12 | 137/391 |
| 2020/0047014 | A1 * | 2/2020 | Whaling | B64D 1/22 | |
| 2025/0052083 | A1 * | 2/2025 | Thomson | E04H 4/12 | |

* cited by examiner

WATER LEVEL MANAGEMENT SYSTEM

BACKGROUND

Pools generally require a particular water level in order to function properly. The appropriate water level ensures efficient drainage and pumping systems, such as by allowing skimmers to ingest surface water at appropriate rates. A proper water level also optimizes the performance of pool pumps and filtration systems, promoting clean and clear water for swimmers. Proper water level also provides an aesthetic factor that makes the pool more enjoyable to see and use.

A typical water level management system monitors the water level and triggers actions to keep it within a specified range. Water level sensors measure the water level and relay this information to a controller. When the water level drops below the desired range, the controller opens a water supply valve to add water to the pool. Similarly, if the water level rises too high, the controller activates a drain valve to release excess water.

A major drawback of the typical water level management system is the electrical power needed. These systems generally draw power by engaging an electronic switch or relay to deliver power to a solenoid valve or other mechanical valve. Typically, these electro-mechanical systems require an inrush current of 500-2000 mA and need about 200-500 mA for operation. This means that the controller is either connected directly to a main power supply or is connected to a pool equipment pad that is capable of supplying this power.

These power requirements are not ideal. They can require installation of various electrical components in order to provide the needed power in a safe manner, especially considering the proximity of these systems to water. These power levels also produce more heat and add cost to the operation of the system.

Furthermore, some water level management systems can suffer from algae growth that obstructs the water level sensor and negatively affects its accuracy and performance. These issues require periodic cleaning of the water level management system, and in some cases rely on a separate water treatment system. To perform better under algae growth conditions, some water level sensors utilize materials and coatings that mitigate algae growth in certain locations. But these features add to the cost of each individual unit.

As a result, a need exists for water level management systems that do not require the electrical infrastructure described above with respect to existing systems. There is also a need for these systems to safely manage potential obstructions, such as algae, to maintain accurate readings over time.

SUMMARY

Examples described herein include systems and methods for improved water level management in a body of water, such as a pool, spa, or pond.

In one example, a water level management system is disclosed, including a water sensor positioned to detect water at a location in a static pipe that is in fluid communication with a body of water. The system further includes a processor that can receive digital signals from the water sensor. It also includes a memory storage and a battery designed to be charged by a low-power data channel.

When the processor receives a signal from the water sensor indicating a low-water-level condition of the body of water, it can cause a fill valve to open, thereby adding water to the body of water. In one aspect, the processor can be programmed to close the fill valve once the water sensor signal indicates that the low-water-level condition of the body of water has resolved, efficiently managing the water level of the body of water and preventing overfill conditions.

In an example, the water level management system can also be configured such that the processor, upon receiving a signal from the water sensor indicating a high-water-level condition of the body of water, can cause a drain valve to open, facilitating the drainage of water from the body of water.

When causing a valve to open or close, the processor can engage an electronic switch and utilize power from the battery to electromechanically open or close the relevant valve. The battery can discharge the needed power and then trickle charge back to a desired charge state, using power supplied through the low-power data channel.

In some instances, both the water sensor and processor can be powered by the low-power data channel, thereby optimizing power consumption and allowing for more efficient and less costly installation techniques.

Additionally, an ultraviolet light can be positioned to illuminate at least a portion of the static pipe. An orientation sensor can be incorporated to prevent eye injuries due to the ultraviolet light when installing, removing, or otherwise performing maintenance on the system. The orientation sensor can block power to the ultraviolet light when indicating an orientation outside of a predefined threshold range. An orientation outside of the threshold range can indicate that a user is handling the system, for example, and during these times the light should not remain illuminated.

The water level management system can be conveniently located within a housing designed to be mounted at an end of the static pipe, offering practical installation and maintenance benefits. Moreover, in certain configurations, all components, including the water sensor, processor, memory storage, and battery, can be solely powered by the low-power data channel, providing a self-contained and energy-efficient solution.

In another aspect, a method for managing the water level of a body of water is disclosed. The method can involve determining, by a water sensor, whether water is present at a location in a static pipe, the static pipe being in fluid communication with the body of water. Based on that determination, a signal can be sent by the water sensor to a processor, the signal indicating a low-water-level condition of the body of water. In response, the processor can cause a fill valve to open, adding water to the body of water. This action can be performed by discharging power from a battery controlled by the processor. For example, the fill valve can be opened or closed by engaging an electronic switch and using power from the battery to electromechanically open or close the valve.

In some instances, the processor can also be configured to cause a drain valve to open based on receiving a signal from the water sensor indicating a high-water-level condition of the body of water, facilitating water drainage when needed. Additionally, the method can include closing the fill valve or drain valve when the processor receives a signal from the water sensor indicating that the low-water-level condition or high-water-level condition, respectively, of the body of water has been resolved, achieving effective water level control.

In one example embodiment, the processor can make determinations based on local weather information. For example, the processor can request weather information from a weather Application Programming Interface ("API") that returns current and/or future weather information. This information can include, for example, expected precipitation over a period of time. In one example, the processor can decide not to fill the pool—even when a low-water-level condition is indicated—based on expected rainfall within the next 48 hours. This can prevent unnecessary water and power usage and avoid having to later drain water from the pool. In some examples, the processor can decide to partially fill the pool based on the expected rainfall. For example, if the water level of the pool is determined to be two inches low, and one inch of rain is expected in the next 24 hours, then the processor can cause the pool to fill one inch and rely on the rain to fill the second inch.

Similar to the system described earlier, the water sensor and processor used in the example method can be powered by the low-power data channel, offering energy efficiency, reduced environmental impact, and convenient installation and integration into existing pool management systems. This low-power data channel can also power the water sensor, processor, and battery can be powered solely by the low-power data channel.

Furthermore, the method can involve powering an ultraviolet light positioned to illuminate at least a portion of the static pipe. Power to the ultraviolet light can be blocked based on an orientation sensor indicating an orientation outside of a threshold range, optimizing power usage and preventing injuries due to the light being directed toward a person's eyes.

In another embodiment, a water level management system is disclosed that uses a water sensor positioned to detect water at a location in a body of water, rather than in a static pipe. The system can include a processor configured to receive digital signals from the water sensor, a memory storage, and a battery designed to be charged by a low-power data channel. In a manner similar to the first example, the processor, based on receiving a signal from the water sensor indicating a low-water-level condition of the body of water, can cause a fill valve to open, effectively adding water to the body of water. The water sensor and processor can be powered by the low-power data channel, offering energy efficiency and extended system operation.

The examples summarized above can each be incorporated into a non-transitory, computer-readable medium having instructions that, when executed by a processor associated with an acid-dispensing device, cause the processor to perform the stages described. Additionally, an acid-dispensing system is disclosed which is configured to perform one or more of the methods disclosed herein.

Both the foregoing general description and the following detailed description are exemplary and explanatory only and are not restrictive of the examples, as claimed.

DESCRIPTION OF THE EXAMPLES

Reference will now be made in detail to the present examples, including examples illustrated in the accompanying drawings.

Examples described herein include systems and methods for improved water level management in a body of water, such as a pool, spa, or pond. An example system includes a water sensor in a static pipe connected to a body of water, a processor receiving signals from the sensor, a memory, and a battery charged via a low-power data channel. When the sensor detects a low-water-level condition, the system opens a fill valve to add water to the body of water. An ultraviolet light can illuminate a portion of the pipe for purposes of preventing algae growth, and an orientation sensor provides a level of safety by deactivating the light for orientations outside a threshold range that could indicate installation or maintenance on the system. In some examples, the system components can all be contained in a housing that can be mounted to an end of the static pipe.

The term "water" is used herein to describe the liquid solution comprising a body of water. It should be understood that the term "water" is not intended to be limited or interpreted strictly. That is, a water-based solution with various chemicals such as chlorine is broadly considered "water" for purposes of this disclosure. Similarly, references to a pool or spa are intended to apply equally to other bodies of water, such as lakes, ponds, aquariums, holding tanks, reservoirs, or any other body of water.

Figure 1:
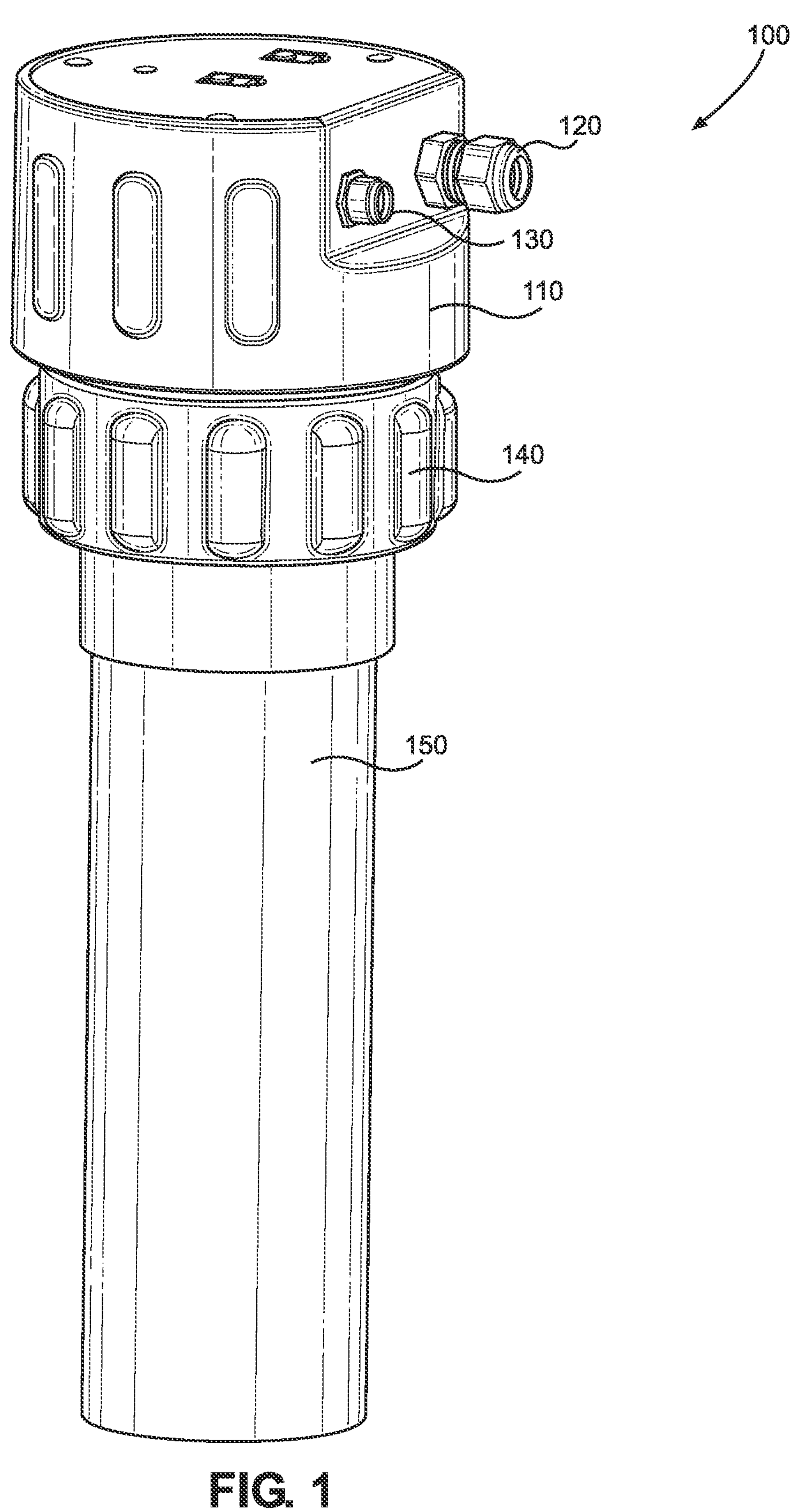
FIG. 1 is a perspective view of an example water level management device attached to a static pipe, according to one or more embodiments herein.

FIG. 1 provides a perspective view of an example water level management device 100 attached to a static pipe 150. As shown the water level management device 100 can include a housing 110 that incorporates various components. In some examples, such as the example of FIG. 1, the housing 110 also includes, or interfaces with, a collar 140. The collar 140 can be configured to mount the water level management device 100 to the static pipe 150.

In an example, the collar 140 can be mounted to the static pipe 150 before installing the housing 110. For example, the collar 140 can be sized for a friction fit around the pipe 150, such that friction (or, optionally, adhesive) can retain the collar 140 on an end of the pipe 150. The collar 140 can also include a portion that extends above the end of the pipe 150 after installation, and that portion can include internal threading. This internal threading can match external threading on a portion of the housing 110, such that the housing 110 can be fastened to the collar 140. During removal or installation, the housing 110 and collar 140 can optionally be installed together as one unit, or in separate stages using the threaded attachment mechanism.

The pipe 150 of FIG. 1 is referred to as a "static" pipe because the pipe 150 is not intended to flow water through it. Instead, this pipe 150 is positioned such that water remains relatively stationary within it, moving only in accordance with movements of the water level of the body of water. For example, if the water level of a pool increases 2 inches based on heavy rainfall during a storm, the water level within the static pipe 150 would similarly increase 2 inches. In this manner, the pipe 150 provides an indication of the water level of the pool without having to measure the pool level directly. This allows flexibility in placing the water level management system, such as in a location hidden from sight and close to a pool controller and other components.

To accommodate changes in the water level of water within the static pipe 150, the housing 110 can include one or more ports or orifices that allow airflow through the housing. This air flow prevents pressure variations within the pipe 150 that could potentially damage components of the water level management device 100 or otherwise produce inaccurate water level readings.

The water level management device 100 can also include one or more couplings 120, 130 for routing power, data, or even chemicals into the water level management device 100. In the example of FIG. 1, the water level management device 100 includes two such couplings 120, 130. At least one of these couplings 120, 130 can receive a low-power data cable from a pool controller. As used herein, the terms "low-power data cable," "low-power data channel," and "data channel" are used interchangeably and intended to generally distinguish data channels from higher-voltage power lines. For example, a power cord plugged into a 120V outlet is not a low-power data channel, but a cable carrying data to or from a 12V-based controller is a low-power data channel. These examples are not intended to be limiting beyond generally distinguishing higher-voltage power-supply lines from data-channel lines. As another example, a channel using an electrical signaling standard such as RS-485 (also known as TIA-485 or EIA-485) or similar can be considered a low-power data channel.

The water level management device 100 can utilize the data channel to send and receive information as well as receive power for charging a battery and powering the various components of the water level management device 100. In some examples, the water level management device 100 can utilize a second coupling 130 for a cable that causes one or more valves to be activated. For example, a first coupling 120 can receive the low-power data channel, while the second coupling 130 can send a signal to an actuator that operates a valve.

By providing a channel directly from the water level management device 100 to the actuator that operates the valve, the water level can be controlled without placing an additional burden on the pool controller. For example, this can allow the water level management device 100 to be installed without modifying the pool controller. In scenarios where the pool controller is sophisticated enough to receive water-level measurements and operate the valves accordingly, then the water level management device 100 can be operated without a dedicated channel from the second coupling 130.

Figure 2:
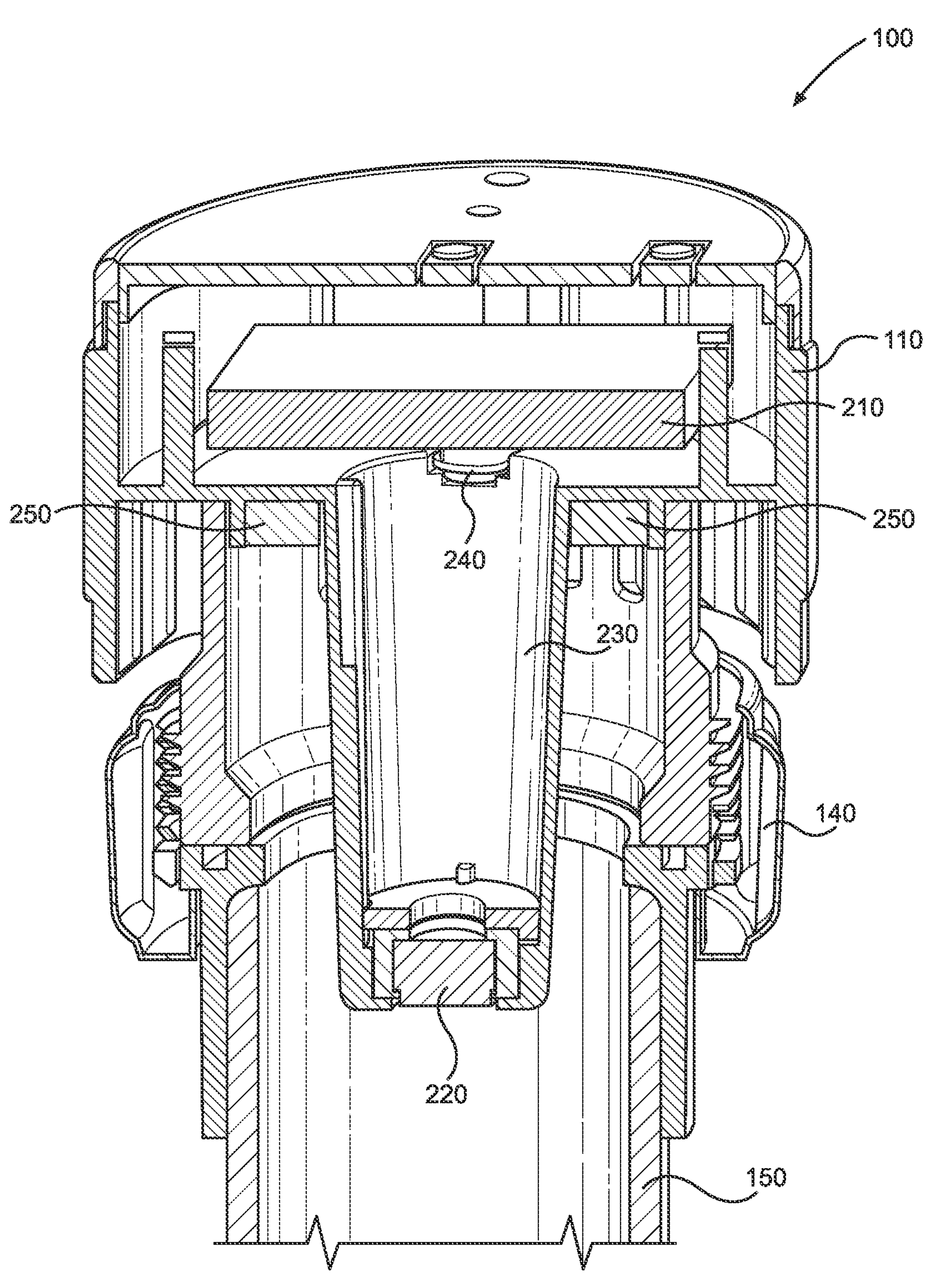
FIG. 2 is a cross-sectional view of the example water level management device of FIG. 1.

FIG. 2 provides a cross-sectional view of the example water level management device 100 of FIG. 1. This cross-sectional view shows a battery 210 positioned in an upper portion of the housing 110. The battery 210 can draw power through a low-power data channel connected to the water level management device 100. Although the current draw can be low, such as 20 mA or 25 mA, this draw is sufficient to trickle charge a battery such as a lithium-ion battery. The battery can then be used later to discharge larger power levels for short periods of times, trickle charging when necessary to retain an acceptable level of charge. For example, the water level management device 100 can draw current from the low-power data channel whenever the battery charge level is below a threshold level, such as 80%, 90%, 99%, or any other charge level.

The cross-sectional view of FIG. 2 also includes a chamber 230. Within the chamber 230 is a temperature sensor 240 intended to measure the temperature of the air within the chamber 230. Based on the proximity to the interior of the pipe 150, the temperature within the chamber 230 can be assumed to be equivalent to the temperature of the air within the pipe 150—a value useful for calculating the water level, as explained in more detail below.

FIG. 2 also shows, at the base of the chamber 230, an ultrasonic transducer 220. Using the ultrasonic transducer 220 and a temperature sensor 240, water level detection can be achieved by measuring the time taken for high-frequency sound waves (ultrasonic waves) to travel to the water surface within the pipe 150 and return as echoes. In this example, the ultrasonic transducer 220 emits the sound waves and receives the reflections, enabling the calculation of the distance between the transducer 220 and the water level. This calculation can be performed by a microprocessor (not shown) within the housing 110.

To ensure accuracy, the temperature sensor 240 measures the ambient temperature, which is vital for compensating for the temperature-dependent speed of sound in air. By accounting for the speed of sound at the given temperature, the time-to-distance data is converted into a precise distance measurement from the transducer 220 to the water surface. Subtracting this distance from the total depth of the pool or tank yields an accurate water level calculation. These calculations can be performed by the microprocessor within the water level management device 100.

In some examples, a humidity sensor is included as well. In addition to temperature effects described above, humidity also has an effect on the speed of sound. A microprocessor within the water level management device 100 can therefore utilize information from both a temperature sensor 240 and a humidity sensor in order to accurately calculate a speed of sound in the air within the measurement area.

In some examples, the transducer 220 sends a first sound wave for purposes of determining a rough depth of the water column within the static pipe 150. The amount of time it takes for the sound wave to return provides information indicative of the rough water level, after compensating for the temperature and humidity of the air in the static pipe 150. If the water level is close to the transducer 220, then a high-energy wave form may produce too much noise to be useful. Similarly, if the water level is far from the transducer 220, a low-energy wave form may not have sufficient power to produce a usable signal. Therefore, based on the first sound wave, the transducer 220 can be tuned to utilize wave forms having a power level appropriate for the current water level.

In some examples, a microprocessor can retrieve a stored table that associates results from the first sound wave with a suggested wave form for subsequent sound waves. After receiving the first sound wave back at the transducer 220, the microprocessor can use the table to look up properties to apply to a subsequent sound wave. This process can be performed iteratively to continue tuning subsequent sound waves and adjust to changing water levels.

The accuracy of the ultrasonic transducer 220 can be negatively affected by debris within the water, which in the context of a static pipe 150 such as the one discussed herein, typically presents itself in the form of algae growth. To prevent such algae growth, the water level management device 100 can include one or more ultraviolet lights 250. These lights 250 can be powered by the battery 210 and can remain on while the device is in an operation state. The lights 250 can be positioned to illuminate the interior of the pipe 150, sterilizing it and preventing debris from growing. In some examples, the lights 250 are ultraviolet light emitting diodes ("LEDs"). However, any light source that provides an algae-preventing light spectrum would be suitable for the application.

While an ultraviolet light source can provide excellent sterilization features, it can also cause potential harm to the human eye if inadvertently directed into the eye. This issue could arise if, for example, an installer applies power to the water level management device 100 before installing the housing 110 on the pipe 150. It could similarly arise during maintenance if the housing 110 is removed from the pipe 150 without first disconnecting the power.

To prevent these types of unwanted eye injuries, the water level management device 100 can include a tilt sensor (not shown) that measures the tilt of the housing relative to a vertical axis generally aligned with the direction of gravity. In these applications, the pipe 150 is provided in a direction concurrent with this vertical axis. When the water level management device 100 is installed on the pipe 150, the tilt sensor should read close to zero—meaning that the water level management device 100 is aligned with the pipe 150. To put this another way, an axis extending through the center of the chamber (through the ultrasonic transducer 220) would be parallel and coaxial to an axis extending along the center of the pipe 150. During these conditions, the water level management device 100 can operate as normal.

However, when the water level management device 100 is removed from the pipe, it potentially can be handled such that the orientation of the water level management device 100 deviates from the operational axis described above. For example, during maintenance the water level management device 100 could be placed on the ground, causing the tilt sensor to calculate a tilt angle close to 90 degrees from the original axis in one example. If a user turns the water level management device 100 upside down to inspect parts within it, then the tilt sensor could read closer to 180 degrees. These are merely examples intended to illustrate what the tilt sensor is measuring.

The microprocessor within the housing 150 can be programmed to perform certain tasks based on a signal received from the tilt sensor. In one example, if the tilt sensor determines that the water level management device 100 is tilted more than 20 degrees from the operational (vertical) axis, the microprocessor can turn the ultraviolet lights 250 off. In this manner, the microprocessor can enforce a threshold operational range. This range can be preprogrammed into the microprocessor in some examples. In other examples, a user can modify the range as desired. There are no limits on this threshold range. For example, the operational range can be 0-5 degrees, 0-10 degrees, 0-45 degrees, or any other range. When the water level management device 100 is tilted outside of the threshold range, the microprocessor can cut power to the light source 250.

Figure 3:
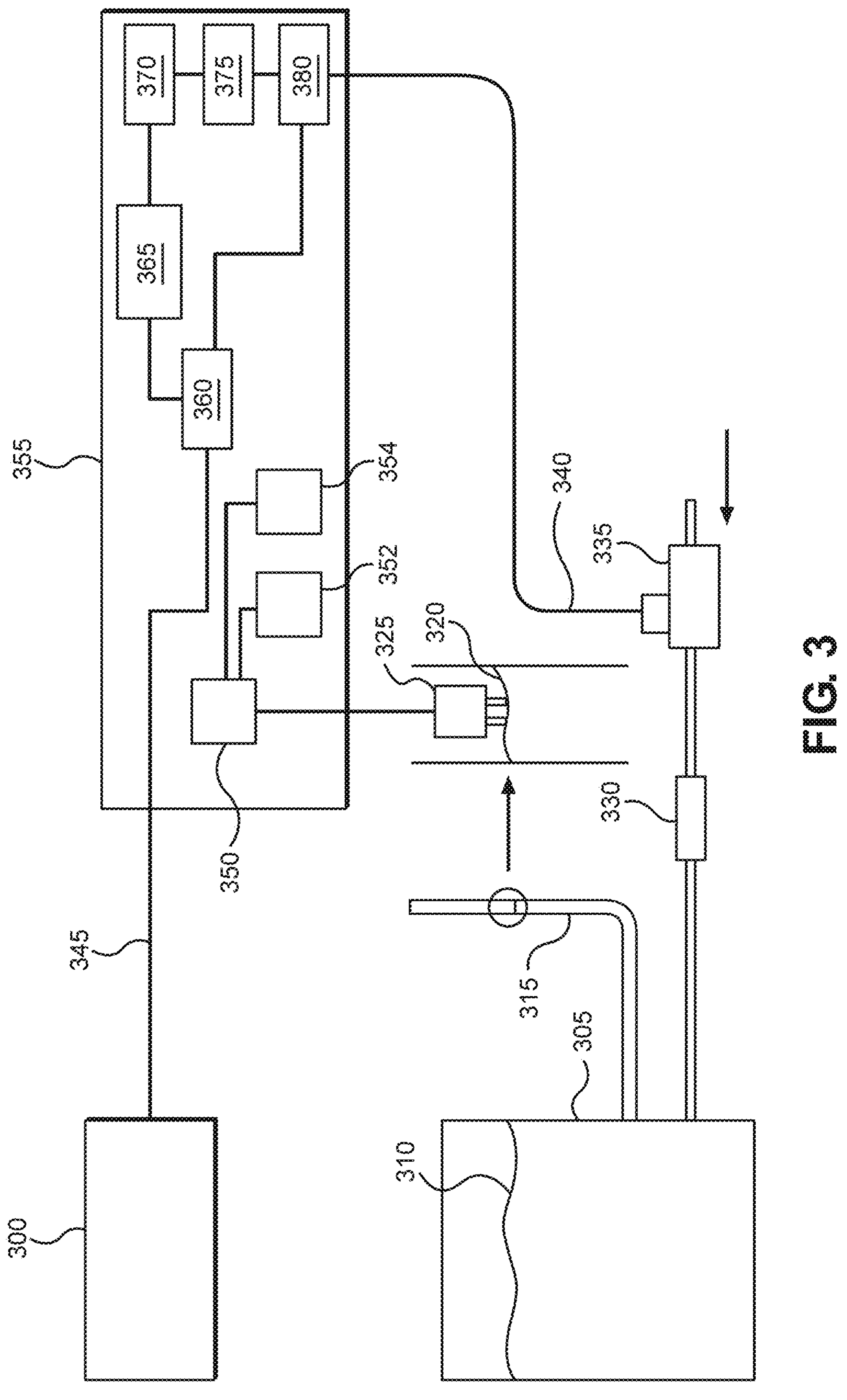
FIG. 3 is a schematic of an example water level management system.

FIG. 3 provides a schematic of an example water level management device 100, such as the device 100 depicted in FIGS. 1 and 2, along with other pool-related components. In the schematic of FIG. 3, the water level management device 100 can be considered elements 355 and 325, along with their respective components. Element 325 represents a water level sensor, which can include at least the ultrasonic transducer 220 of FIG. 2 in an example. Element 355 can be considered the remaining components of the water level management device 100.

Element 300 corresponds to a pool controller that can control various different aspects of the operations related to a pool 305. The pool controller 300 can communicate with various components using one or more data channels. A typical type of such data channel is an RS485 bus. In the example of FIG. 3, the data channel 345 connects the pool controller 300 to a bus interface unit 360 within the water level management unit 355. The bus interface unit 360 can direct power to a battery charging circuit 365, which can function as a current limiter that caps the current drawn while charging a battery.

Based on an instruction from the microcontroller 350 (also interchangeably referred to herein as a "processor" or "microprocessor") of the water level management unit 355, the bus interface unit 360 can provide power to an electronic switch 380 that opens or closes a valve elsewhere in the system. As part of this process, the battery can utilize a current limiter 370 and a boost regulator to boost voltage to a level sufficient to operate an actuator associated with a valve. Although not shown in the drawing, the microcontroller 350 can be in electrical communication with one or more of the bus interface unit 360, electronic switch 380, battery, and any other electrical components of the water level management unit 355. As shown in FIG. 3, the microcontroller 350 can interface with a memory storage 352 for storing non-transitory, computer-readable media. FIG. 3 also shows an orientation sensor 354 described further with respect to FIG. 4, where the orientation sensor 354 is configured to indicate an orientation of the unit 355 and, if the orientation is outside of a threshold range, cause power to not be provided to an ultraviolet light.

The microcontroller 350 can also be in electrical communication with the water sensor 325, as shown. The water sensor 325 can be positioned proximate to a static pipe 315 that includes a pipe water level 320 to be detected. The pipe water level 320 can correspond to a pool water level 310 based on being in fluid communication with the pool 305. Using techniques described previously, the water sensor 325 can collect information corresponding to a water level and report that information to the microcontroller 350. Based on the status of the water level, the microcontroller can either take no action, cause a fill valve to open, or cause a drain valve to open.

In the example of FIG. 3, the water level management unit 355 is in communication with a fill valve unit 335. The fill valve unit 335 can include a valve and an actuator for opening and closing that valve. When power is received at the actuator via element 340, the actuator can open or close the valve. As shown by the directional arrow, the water flows toward the pool when the fill valve unit 335 is open. The water can pass through a check valve 330 before entering the pool 305.

In another example, not shown, the water level management unit 355 can perform a similar action to a drain valve unit. That is, the unit 355 can apply power to an actuator that opens a drain valve, allowing water to drain from the pool 305.

In one example embodiment, the microcontroller 350 can make determinations based on local weather information. For example, the microcontroller 350 can request weather information from a weather Application Programming Interface ("API") that returns current and/or future weather information. This information can include, for example, expected precipitation over a period of time. In one example, the microcontroller 350 can decide not to fill the pool—even when a low-water-level condition is indicated—based on expected rainfall within the next 48 hours. This can prevent unnecessary water and power usage and avoid having to later drain water from the pool. In some examples, the microcontroller 350 can decide to partially fill the pool based on the expected rainfall. For example, if the water level of the pool is determined to be two inches low, and one inch of rain is expected in the next 24 hours, then the microcontroller 350 can cause the pool to fill one inch and rely on the rain to fill the second inch.

The microcontroller 350 can receive feedback from the water level sensor 325 before, during, and after a filling or draining operation. This allows the microcontroller 350 to determine precisely when to open or close a valve. For example, if the microcontroller 350 determines, based on information from the water level sensor 325, that the water level of the pool 305 is two inches below the ideal level, it can cause a fill valve to open. The fill valve may cause the pool level to rise one inch per hour in this example. During the filling process, the microcontroller 350 can receive periodic or continuous updates from the water level sensor 325 indicating a more recent water level measurement. Using this feedback, the microcontroller 350 can wait until the water level is at a desired level before providing an instruction to close the valve. A similar feedback loop can be utilized for draining excess water from the pool.

The microcontroller 350 can also keep track of water consumption over time. It can be programmed to alert the pool controller 300 in a situation where excess water is being consumed, which can indicate a leak in the system. For example, the microcontroller 350 can be programmed to allow for typical rates of evaporation and water loss from use, which can be calculated based on statistics from other pools in the same area. If the rate of water loss exceeds this level by a threshold amount, the microcontroller 350 can alert the pool controller 300, which in turn can notify a user or take other remedial actions as necessary for the situation.

In some examples, the microcontroller 350 can determine a short circuit condition or other fault in one or more components related to the systems described herein. For example, the feedback loop described above can indicate that no filling is occurring even though the appropriate commands have been sent. This can be caused by, for example, a solenoid, valve actuator, or motor having a short circuit or other physical fault. In such scenarios, the microcontroller 350 can cause an alert to be generated, which in turn can notify a user of the condition.

This feedback loop can also be used to determine that the pool includes a negative edge, where water spills over the edge. In such pools, the water level cannot be raised above the negative edge. If the microcontroller 350 is attempting to fill up the pool beyond the level of the negative edge, it can result in significant water waste. To avoid this, the microcontroller 350 can learn that the fill process stalls at a certain water level each time, indicating that the pool has a negative edge at that level. Based on this determination, the microcontroller 350 can adjust the desired fill level based on the negative edge.

Figure 4:
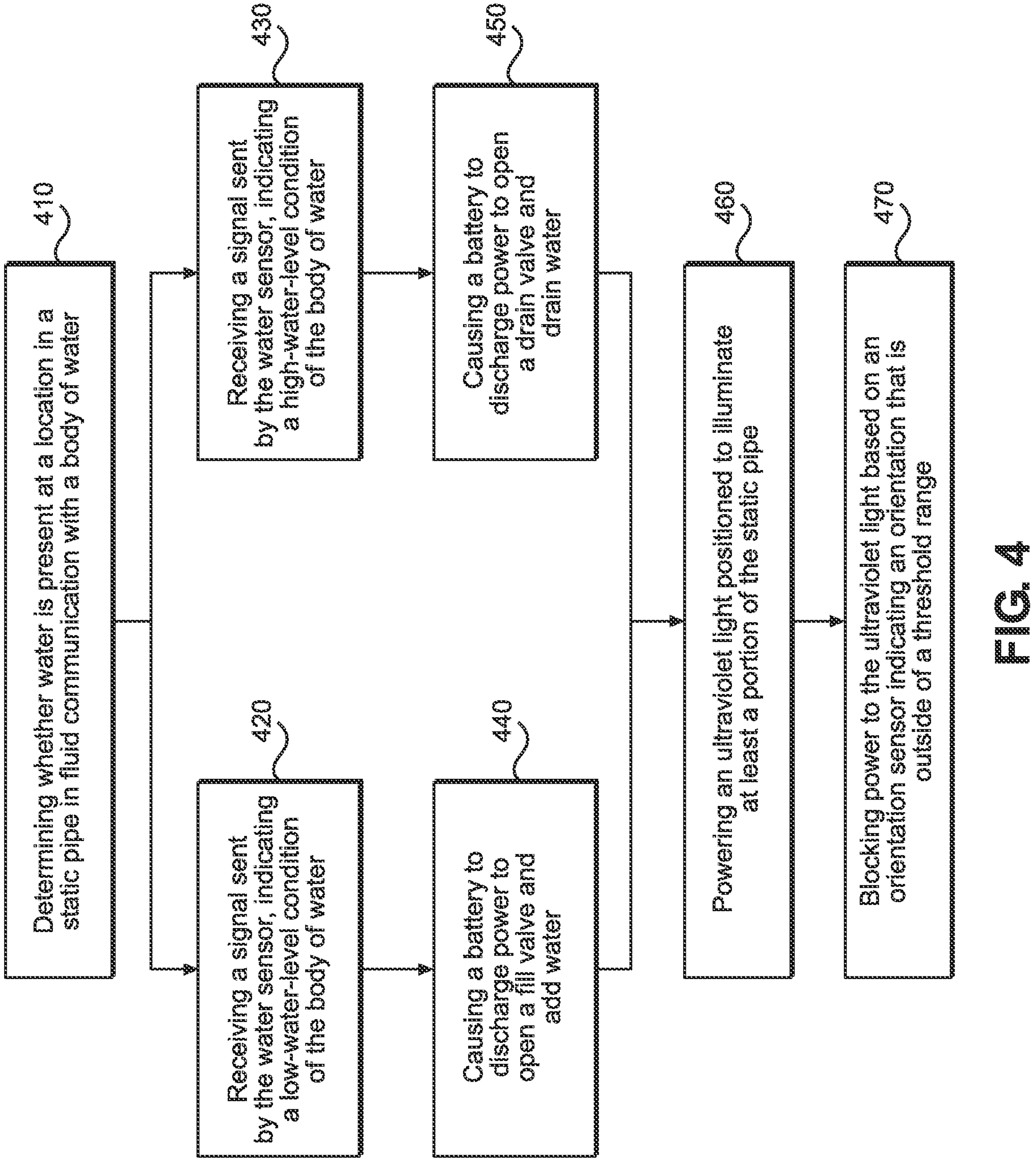
FIG. 4 is a flowchart of an example method for using a water level management to add or remove water from a body of water.

FIG. 4 provides a flowchart of an example method for using a water level management to add or remove water from a body of water. For ease of understanding, element numbers referencing components discussed above are omitted in the discussion of FIG. 4 unless specifically referencing back to previous drawings. However, the components discussed in FIG. 4 should be presumed to refer to elements of FIGS. 1-3 discussed above, unless specifically indicated otherwise.

At stage 410, a water level management system can determine whether water is present at a location in a static pipe in fluid communication with a body of water. Said another way, the water level management system can determine a water level with the static pipe. For example, using an ultrasonic transducer and a temperature sensor, water level detection can be achieved by measuring the time taken for high-frequency sound waves (ultrasonic waves) to travel to the water surface within the pipe and return as echoes. In this example, the ultrasonic transducer emits the sound waves and receives the reflections, enabling the calculation of the distance between the transducer and the water level. This calculation can be performed by the microprocessor.

To ensure accuracy, a temperature sensor measures the ambient temperature, which is vital for compensating for the temperature-dependent speed of sound in air. By accounting for the speed of sound at the given temperature, the time-to-distance data is converted into a precise distance measurement from the transducer to the water surface. Subtracting this distance from the total depth of the pool or tank yields an accurate water level calculation. These calculations also can be performed by the microprocessor within the water level management device.

Based on the signal received from the water sensor, the microprocessor can determine that the relevant body of water is at an acceptable level, a low-water level, or a high-water level. For example, stage 420 includes receiving a signal from the water sensor where the signal indicates a low-water-level condition of the body of water. In that example, the method proceeds to stage 440, where the microprocessor causes a battery within the water level management system to discharge power to open a fill valve and add water to the pool.

Alternatively, stage 430 can include receiving a signal from the water sensor where the signal indicates a high-water-level condition of the body of water. In this example, the method proceeds to stage 450, where the microprocessor causes the battery to discharge power to open a drain valve and remove water from the pool.

Both of these processes are described in more detail above and can be precisely controlled by the microcontroller using a feedback loop. This allows the microcontroller to fill or drain the pool to the appropriate level before closing the valve.

Stage 460 can be performed before, after, and/or during any of stages 410-450. Stage 460 can include powering an ultraviolet light source positioned to illuminate at least a portion of the static pipe. In practice, this portion of the pipe will include the area of the pipe in proximity to the water level sensor. As explained above, the ultraviolet light source can sanitize the pipe and prevent algae growth or other sources debris that can negatively affect the accuracy of the water level sensor.

At stage 470, the microprocessor can block power to the ultraviolet light source based on an orientation sensor (also referred to herein as a tilt sensor) indicating an orientation of the water level management device that is outside of a threshold range. In one example, if the tilt sensor determines that the water level management device is tilted more than 20 degrees from the operational (vertical) axis, the microprocessor can turn the ultraviolet lights off. In this manner, the microprocessor can enforce a threshold operational range. This range can be preprogrammed into the microprocessor in some examples. In other examples, a user can modify the range as desired. There are no limits on this threshold range. For example, the operational range can be 0-5 degrees, 0-10 degrees, 0-45 degrees, or any other range. When the water level management device is tilted outside of the threshold range, the microprocessor can cut power to the light source.

Other examples of the disclosure will be apparent to those skilled in the art from consideration of the specification and practice of the examples disclosed herein. Though some of the described methods have been presented as a series of steps, it should be appreciated that one or more steps can occur simultaneously, in an overlapping fashion, or in a different order. The order of steps presented are only illustrative of the possibilities and those steps can be executed or performed in any suitable fashion. Moreover, the various features of the examples described here are not mutually exclusive. Rather any feature of any example described here can be incorporated into any other suitable example. It is intended that the specification and examples be considered as exemplary only, with a true scope and spirit of the disclosure being indicated by the following claims.

What is claimed is:

1. A water level management system, comprising:

a water sensor positioned to detect a water level within a static pipe, the static pipe being in fluid communication with a body of water;

a processor configured to receive digital signals from the water sensor;

a memory storage;

a battery configured to be charged by a low-power data channel;

an ultraviolet light positioned to illuminate at least a portion of the static pipe; and an orientation sensor that blocks power to the ultraviolet light based on the orientation sensor indicating an orientation that is outside of a threshold range, wherein the processor is configured to, based on receiving a signal from the water sensor indicating a low-water-level condition of the body of water, cause a fill valve to open such that water is added to the body of water.

2. The water level management system of claim 1, wherein the processor is also configured to, based on receiving a signal from the water sensor indicating a high-water-level condition of the body of water, cause a drain valve to open such that water is drained from the body of water.

3. The water level management system of claim 1, wherein the water sensor and processor are powered by the low-power data channel.

4. The water level management system of claim 1, wherein the water sensor, processor, memory storage, and battery are located within a housing that is configured to be mounted to an end of the static pipe.

5. The water level management system of claim 1, wherein the processor is configured to analyze a change in water level based on an attempt to fill the pool, and determine that a short-circuit condition or other fault exists in the system.

6. The water level management system of claim 1, wherein the processor is configured to, based on receiving a signal from the water sensor indicating that the low-water-level condition of the body of water has resolved, cause the fill valve to close.

7. The water level management system of claim 1, wherein causing the fill valve to open comprises engaging an electronic switch and using power from the battery to electromechanically open the fill valve.

8. A method for managing a water level of a body of water, the method comprising:

determining, by a water sensor, the water level in a static pipe, the static pipe being in fluid communication with the body of water;

receiving, at a processor, a signal sent by the water sensor, the signal indicating a low-water-level condition of the body of water; and causing, by the processor, a fill valve to open such that water is added to the body of water;

wherein causing the fill valve to open includes discharging power from a battery controlled by the processor, and wherein determining the water level comprises sending a first sound wave and, based on measuring a return of the first sound wave, sending a second sound wave having a different amplitude than the first sound wave.

9. The method of claim 8, wherein the processor is also configured to, based on receiving a signal from the water sensor indicating a high-water-level condition of the body of water, cause a drain valve to open such that water is drained from the body of water.

10. The method of claim 8, wherein the water sensor and processor are powered by a low-power data channel.

11. The method of claim 8, further comprising powering an ultraviolet light positioned to illuminate at least a portion of the static pipe.

12. The method of claim 11, further comprising blocking power to the ultraviolet light based on an orientation sensor indicating an orientation that is outside of a threshold range.

13. The method of claim 8, wherein the water sensor, processor, and battery are located within a housing that is configured to be mounted to an end of the static pipe.

14. The method of claim 8, wherein the water sensor, processor, and battery are all powered by a low-power data channel.

15. The method of claim 8, further comprising causing the fill valve to close based on the processor receiving a signal from the water sensor indicating that the low-water-level condition of the body of water has resolved.

16. A water level management system, comprising:

a water sensor positioned to detect a water level of a body of water, the water sensor configured to send a first sound wave and, based on measuring a return of the first sound wave, send a second sound wave having a different amplitude than the first sound wave;

a processor configured to receive digital signals from the water sensor;

a memory storage;

a battery configured to be charged by a low-power data channel; and an ultraviolet light positioned to illuminate at least a portion of the static pipe, wherein the processor is configured to, based on receiving a signal from the water sensor indicating a low-water-level condition of the body of water, cause a fill valve to open such that water is added to the body of water.

17. The water level management system of claim 16, wherein the water sensor and processor are powered by the low-power data channel.

* * * * *